US00PP08175P

United States Patent [19]

Saville

[11] Patent Number: Plant 8,175

[45] Date of Patent: Mar. 16, 1993

[54] MINIATURE ROSE PLANT NAME SAVACHILD

[75] Inventor: F. Harmon Saville, Rowley, Mass.

[73] Assignee: Nor'East Miniature Roses, Inc., Rowley, Mass.

[21] Appl. No.: 740,500

[22] Filed: Aug. 5, 1991

[51] Int. Cl.[5] ..... A01H 5/00

[52] U.S. Cl. ..... Plt./7.1

[58] Field of Search ..... Plt. 2, 7.1

[56] References Cited

U.S. PATENT DOCUMENTS

P.P. 4,597 9/1980 Meredith et al. ..... Plt. 7.1

*Primary Examiner*—Howard J. Locker

*Attorney, Agent, or Firm*—Christie, Parker & Hale

[57] ABSTRACT

A new miniature rose with deep pink and white picotee flowers of good form.

1 Drawing Sheet

SUMMARY OF THE INVENTION

The present invention relates to a new and distinct variety of rose plant of the miniature rose class, which was created by me by crossing as seed parent an unnamed, unpatented seedling of my creation and as pollen parent the rose known as "Party Girl" (U.S. Plant Pat. No. 4,598). The varietal denomination of this new rose is "Savachild".

Among the novel characteristics possessed by this new variety which distinguishes it from its parent and all other varieties of which I am aware is its unusual deep pink and white picotee flowers of good form and which opens well to result in an attractive open bloom.

Asexual reproduction by propagation by cuttings of the new variety as performed in Essex County, Mass. shows that the foregoing and other distinguishing characteristics come true to form and are established and transmitted through succeeding propagations.

BRIEF DESCRIPTION OF ILLUSTRATION

The accompanying illustration shows typical specimens of the flowers of the new variety in different stages of development depicted in color as nearly true as it is reasonably possible to make the same in a color illustration of this character.

DETAILED DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart.

Parentage:

*Seed parent.*—Unnamed seedling.

*Pollen parent.*—"Party Girl".

Class: Miniature.

The following observations are made of specimens grown under glass in Essex County, Mass., during the month of November.

FLOWER

Blooming habit: Continuous.

A. Bud:

(1) *Size.*—Medium.

(2) *Form.*—High centered, pointed, ovoid.

(3) *Color.*—As sepals divide, bud color is near 155A-D with near 54A-B at petal edge.

(4) *Sepals.*—Smooth, longer than bud.

(5) *Peduncle.*—Length — about ¾-inches. Aspect — straight. Strength — erect. Color — near 144A.

B. Bloom:

(1) *Size.*—Average size when fully expanded — about 1¾ inches.

(2) *Borne.*—Singly, one to a stem and several together in large sprays.

(3) *Form*—High centered at first becoming flat; outer petals remaining at first loosely rolled under and some quill to points; outer petals tend to have curved apices.

(4) *Petalage.*—Number of petals under normal conditions — about 18 to 22.

(5) *Color.*—After sepals fall and petals unfurl, predominant flower color of visible petal undersurface is near 155A-D flushed with pink and near 52A-B to 54A-B at and near petal edges. Flowers retain the picotee bi-coloration of near white with pink edging as they open. Deeper hues may be seen where petals bunch but pink coloration remains only at petal edges. Consistent bi-coloring remains after three or more days with slight lightening of the pink coloration. General tonality from a distance is a pink and white bi-color. Color at point of petal attachment is near 4C. Open bloom displays attractive picotee pink-edged white coloration with pink stigmas and a pinkish beige stamens visible at flower centers.

C. Petals:

(1) *Texture.*—Thick.

(2) *Appearance.*—Inside velvety and outside satiny.

(3) *Form.*—Fan shaped; some pointed apices; outer petals wider than inner petals.

(4) *Arrangement.*—Regularly arranged, imbricated.

(5) *Petaloids in center.*—Few to none.

(6) *Persistence.*—Average.

(7) *Fragrance.*—Slight.

(8) *Lasting quality.*—Lasting quality on plant and after cutting is average.

REPRODUCTIVE ORGANS

A. Stamens, filaments and anthers:

*Arrangement.*—Regularly arranged around styles.

*Color.*—Near 25C.

B. Pollen:

*Color.*—Near 25B.

C. Styles: Tin, medium length.

D. Stigmas:

*Color.*—Near 53C.

E. Hips: None observed.

PLANT

A. Form: Upright.

B. Growth: Very vigorous, uniform branching.

*Height attained.*—About 18 to 24 inches.

C. Foliage: Compound 5 to 7 leaflets.

(1) *Size.*—Medium.

(2) *Quantity.*—Abundant.

(3) *Color.*—New foliage: Upper side — near 139A to 139B. Under side — near 139C. old foliage: Upper side — near 139A. Under side — near 139C.

(4) *Shape.*—Oval, pointed.

(5) *Texture.*—Upper side is semi-glossy; under side is matte.

(6) *Edge.*—Serrate.

(7) *Serration.*—Regular, deeper toward apex.

(8) *Leaf stem.*—Color — near 143A. Under side — 143A.

(9) *Stipules.*—Medium length, slightly bearded.

(10) *Resistance to disease.*—Blackspot — Good. Mildew — Good. Rust — Good.

D. Wood:

(1) *New wood.*—Color — near 143C. Bark — smooth.

(2) *Old wood.*—Color — near 141A. Bark — smooth.

E. Thorns:

*Quantity (main stalk).*—Ordinary.

*On laterals from stalk.*—Ordinary.

*Form.*—Long, thin.

*Length.*—Medium.

*Color.*—Near 145C/181D at base.

*Position.*—Irregular.

*Prickles.*—None.

F. Winter hardiness: Needs protection in severe climates.

I claim:

1. A new and distinct variety of rose plant of the miniature rose class, substantially as shown and described.

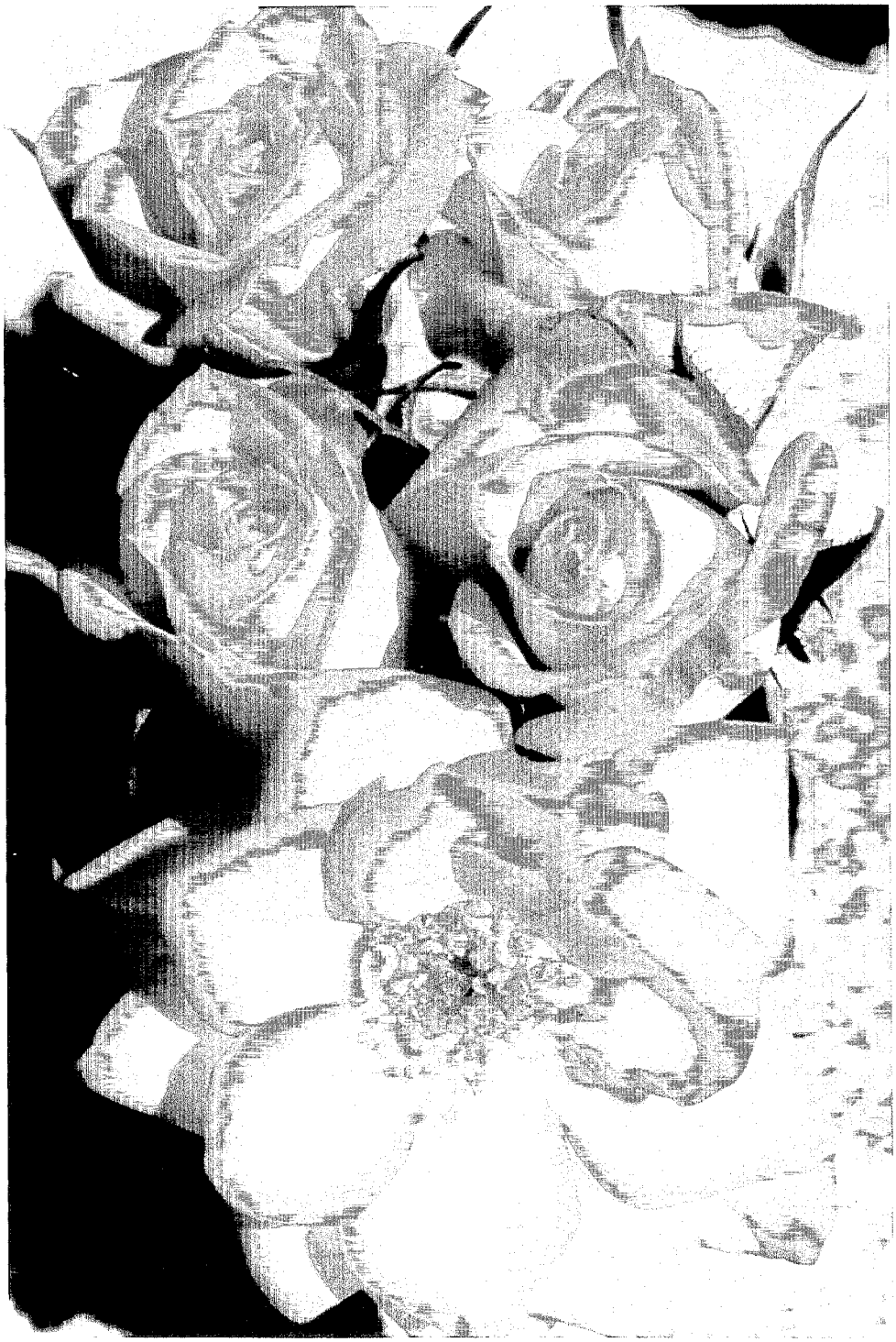

* * * * *